United States Patent [19]
Wagoner, III

[11] Patent Number: 5,090,421
[45] Date of Patent: * Feb. 25, 1992

[54] APPARATUS FOR TESTING MUSCLE STRENGTH

[75] Inventor: Earl V. Wagoner, III, West Jordan, Utah

[73] Assignee: Hoggan Health Industries, Inc., Draper, Utah

[*] Notice: The portion of the term of this patent subsequent to Mar. 10, 2006 has been disclaimed.

[21] Appl. No.: 939,809

[22] Filed: Dec. 9, 1986

[51] Int. Cl.$^5$ ............................................. A61B 5/22
[52] U.S. Cl. ................................. 128/774; 128/782; 73/862.04; 73/379
[58] Field of Search ............... 128/774, 782; 73/379, 73/862.04

[56] References Cited

U.S. PATENT DOCUMENTS

| | | | |
|---|---|---|---|
| 3,359,789 | 12/1967 | Forse | 73/862.65 |
| 3,561,280 | 2/1971 | MacPhee et al. | 73/862.04 |
| 3,680,386 | 8/1972 | Cannon | 128/774 |
| 4,501,148 | 2/1985 | Nicholas | 73/379 |
| 4,616,511 | 10/1986 | Gindy et al. | 73/862.04 |

Primary Examiner—Kyle L. Howell
Assistant Examiner—John Hanley
Attorney, Agent, or Firm—Mallinckrodt & Mallinckrodt

[57] ABSTRACT

Apparatus for use in testing muscle strength comprising a transducer including strain gauges mounted to provide deflection readings that will be accurate for even different directions of force application and read out apparatus receiving strain gauge data and for displaying output data indicative of muscle strength.

3 Claims, 4 Drawing Sheets

APPARATUS FOR TESTING MUSCLE STRENGTH

BRIEF DESCRIPTION OF THE INVENTION

Field of the Invention

This invention relates to the measuring of muscle strength.

BACKGROUND OF THE INVENTION

There has long been a need for devices to accurately measure muscle strength and to provide data regarding changes in muscle strength of subjects on which such apparatus is used. Physical therapists, athletic trainers and orthopedic surgeons, for example, need such apparatus to accurately moniter a patient's history and to systematically test for muscle improvements.

Muscle testing is an integral and important part of a complete physical exam since it provides information not otherwise obtained that is useful in differential diagnosis, prognosis and treatment of neuromuscular and musculoskeletal disorders. A knowledge of the relative strengths of the various muscles of the body provides a foundation for rehabilitation and strengthening of the muscles in a programmed manner that will give maximum overall fitness. Knowledge of the strengths of muscles before and after administration of certain drugs such as cholinergic drugs may also assist in determining the type and nature of medications and other treatments subsequently used to treat progressive muscular weaknesses such as myasthenia gravis.

PRIOR ART

A number of devices have been proposed in the past to provide for muscle testing and for measuring various characteristics of muscles. Some of these known devices are shown, for example, in U.S. Pat. Nos. 3,482,564, issued to Robinson; 3,680,386, issued to Cannon; 3,690,208, issued to Daniels; 3,752,144, issued to Weigle, Jr.; 3,916,876, issued to Freeman; and 4,337,780, issued to Metrick. The aforesaid devices utilize a variety of transducers to transmit muscular pressure application to different kinds of readout and recording devices. These devices, in general, strive to obtain accurate input, accurate repeat readings during subsequent test periods, and a temporary or permanent record display indicative of the results obtained. Several of the devices use transducers incorporating fluid filled bags or cylinders and others use spring-loaded pressure sensors.

Several of the patents identified above disclose the use of frameworks for positioning a test subject such that exact duplication of test conditions will be obtained during subsequent tests. The apparatus of others of the patents use harnesses or other structures in an attempt to position the apparatus on a test subject so that identical test conditions are established for a plurality of tests.

A muscle testing system incorporating a manually held pressure input transducer connected by a cable and a microprocessor to a digital readout display has been advertised under the trademark "MYO-METRIC II" by Mycron Medical, Inc., Fayetteville, Ark. The MYO-METRIC II unit uses a twin element bridge type of pressure transducer, with an air bag configuration, and requires consistent placement against a subject user's body if the muscles of the body are to be monitered on a continuing basis.

To the best of my knowledge there has not heretofore been available a testing system having a force sensor or transducer that will accurately measure minute pressure changes; that will perform accurately even if force application inputs are applied at different angles, to thereby give accurate repeat measurements during subsequent test periods, even if certain exact test conditions are not duplicated; and to provide both an immediately observable readout showing test results, comparison of present with past test results, and permanent copies of such readout for use by the subject being tested, the persons conducting the tests, and others.

Principal objects of the present invention are to provide a muscle strength measuring device having a force input transducer that will provide accurate measurements of muscle strength, even when used for repeat tests, without the necessity for accurate positioning of the transducer on a point relative to a body part containing a muscle being tested.

Other objects are to provide a force input transducer that is coupled to a computer programmed to provide both immediate screen display and permanent display of the muscle strength detected by the transducer; display of comparative test results from a plurality of tests; display of test results as compared with desired conditions; and other date useful to the subject being tested and to others.

FEATURES OF THE INVENTION

Principal features of the present invention include a force input transducer having a hand-held transducer housing with a support shaft rigidly attached to and projecting from a cantilevered support arm located within the transducer housing. A cushion is provided on one face of the transducer housing as a support surface for a tester and a strap at the opposite face for securing the housing to the hand of a tester.

The support shaft is threaded to receive correspondingly interiorly threaded pressure plates shaped to conform to selected body portions of the subject being tested.

A plurality of strain gauges are mounted to the support shaft and the cantilevered support arm in a pattern such that force application to an attached pressure plate, regardless of the direction of such force application, will be accurately measured as indicative of muscle strength.

The strain gauges are connected through a digital information processor circuit to a computer programmed to display readings obtained, a comparison of current and past readings, and a comparison of past and current readings against desired results and to provide hard copy history and text results for use by subjects being tested, therapists, doctors or others having an interest in such test results.

Other objects and features of the invention will become apparent from the following detailed description and drawings disclosing what is presently contemplated as being the best mode of the invention.

THE DRAWINGS

In the drawings:

FIG. 1 is a somewhat schematic elevation view of the transducer apparatus of the invention;

FIG. 2, an axial vertical section through the pressure input transducer device of the invention;

FIG. 3, a perspective view of an alternate pressure plate of the invention;

FIG. 4, a view like that of FIG. 3, but showing another embodiment of pressure plate;

FIG. 5, a view like that of FIG. 3, but showing still another embodiment of pressure plate;

FIG. 6, a schematic diagram of a typical circuit used with the device of the invention;

FIG. 7, a schematic front elevational view of an isolated transducer arrangement of the invention;

FIG. 8, a side elevational view of the transducer arrangement of FIG. 7;

FIG. 9, a top plan view of the transducer arrangement of FIG. 7 showing placement of the strain gauges;

FIG. 10, a representation of an isolated post to which a pressure plate is attached and the x-y designations for stress, strain, and moment measurements;

FIG. 11, a representation of an isolated cantilever bar to which a post is attached and the x-y designation for stress, strain, and moment measurements;

FIG. 12, the isolated cantilever bar of FIG. 11 showing preferred dimensions;

FIG. 13, the isolated post of FIG. 10 indicating a preferred diametrical dimension; and FIG. 14, a top plan view of the transducer arrangement of FIG. 7 showing examples of various possible moment lever arms for calculation purposes.

DETAILED DESCRIPTION

Figure 1:
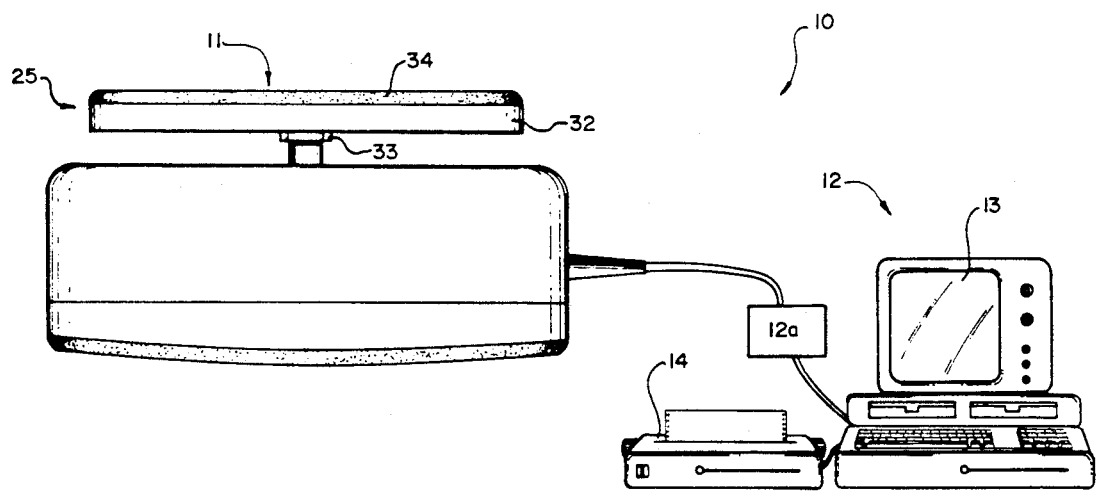
Figure 2:
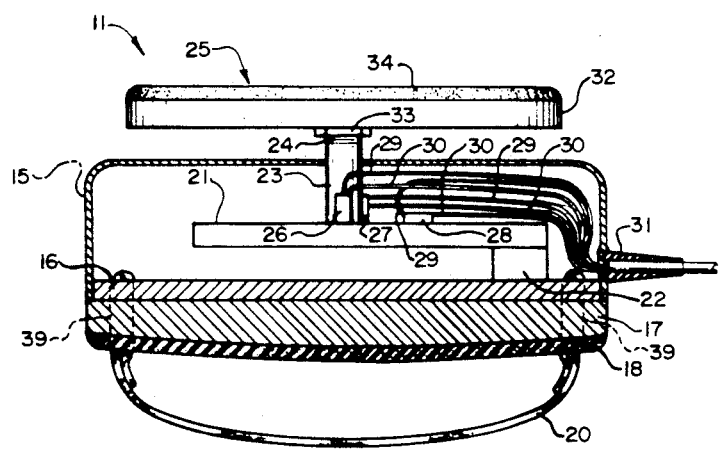

Referring now to the drawings:

In the illustrated preferred embodiment, the apparatus of the invention, shown generally at 10, includes a pressure input transducer device 11, a computer 12 having a display screen 13, and a printer 14.

The input transducer device 11 includes a transducer housing 15 having a rigid plate forming a base 16 therefor. A cap 17 having a cushioned pad 18 thereon is fixed to the exterior face of the base 16 and a resilient strap 20 extends over the cushioned pad 18.

A substantially rigid support arm assembly 21 has an integral leg 22 affixed to the base 16 and a support arm cantilevered from the leg 22, above the base 16.

A substantially rigid support post 23 is affixed to and extends exteriorly of housing 15, and from the arm 21 and is threaded at 24 on its free, exterior end to receive a pressure plate 25.

A strain gauge 26 is bonded to one side of the support post 23 and a second strain gauge 27 is bonded to the support post ninety degrees (90°) turned from the first strain gauge 26. A third strain gauge 28 is bonded on the centerline of the support arm 21 and in the central plane of gauge 27. The usual electrical lead wires 29 and 30 are respectively attached to opposite ends of each of the strain gauges and then extend out of housing 15 at 31 to be connected to the computer 12, through digital information processor circuit 12a.

The pressure plate 25 comprises a rigid disk 32 from which a centrally positioned, interiorly threaded boss 33 extends. A contact layer 34 of plastic or other suitably textured and easily cleaned material covers the face of plate 25 opposite boss 33 to serve as a contact surface against the skin of a subject user of the device.

Figure 5:
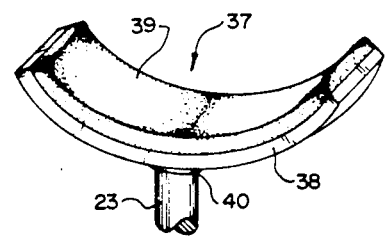
Figure 3:
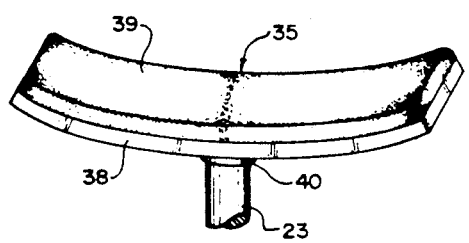
Figure 4:
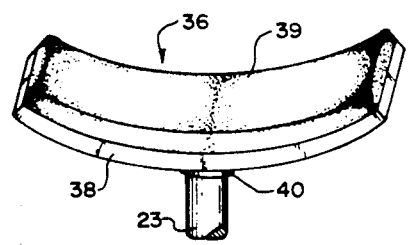

The disk-shaped pressure plate 25 is suitable for application to many body parts for muscle testing, but pressure plates having other shaped surfaces for even better application to some body parts may be used in place of the pressure plate 25. The pressure plates 35, 36 and 37, shown respectively in FIGS. 3, 4 and 5, each include an elongate, curved, substantially rigid disk 38 and a contact layer 39 on the inner curve thereof. An interiorly threaded boss 40 extends from the outer curve side of the disk 38 to allow the pressure plates to be attached to post 23 in place of plate 25. Each of the plates 35, 36 and 37 has a different degree of curvature than does the other plates so that each plate is better adapted to contact with various body portions.

The resilient strap 20 has its ends inserted through slots 39 in the base plate and folded back and sewn to prevent pullout of the strap from the housing.

Figure 6:
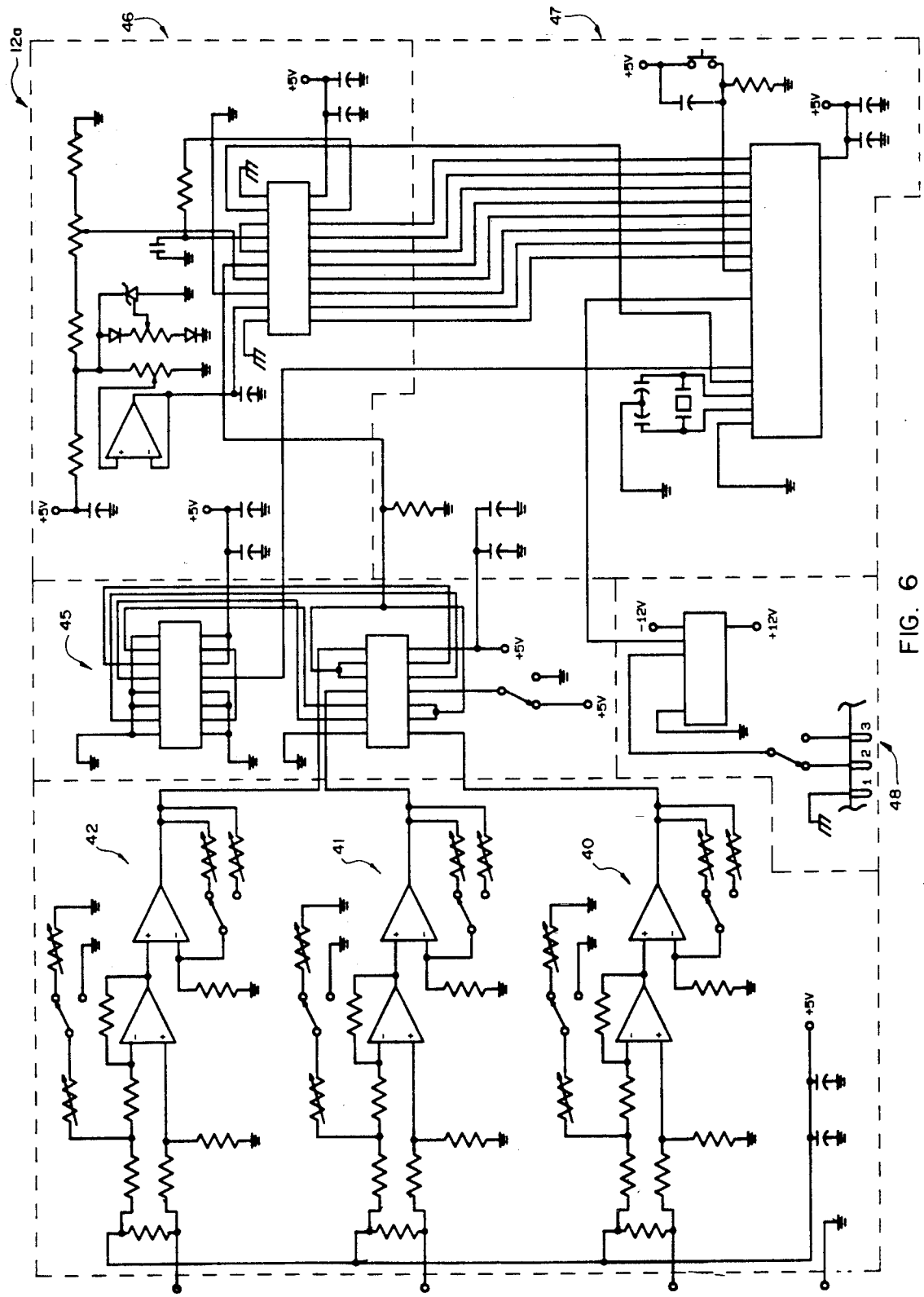

The strain gauges 26, 27 and 28 are preferably monolithic silicon gauges each having a longitudinal axis. The longitudinal axes of gauges 26 and 27 are aligned with the central longitudinal axis through the support post 23 and the longitudinal axis of support arm 21. The strain gauges 26, 27 and 28 are connected by pairs of lead wires 29 and 30 and a separate electric circuit to signal condition circuits 40, 41 and 42, respectively FIG. 6 and, to a multiplexer and counter circuit 45 of the digital information processor circuit 12a.

The multiplexer and counter circuit 45 is connected through an A to D convertor 46 to a processor 47, and the processor is coupled by an interface driver 48 to a computer.

With the axes of the strain gauges arranged in the manner described above, any force application to the pressure plate being used will provide a correct load reading regardless of the location or angle of force applied to the pressure plate.

Mathematical verification of the accuracy of the readout of the testing device of the invention is shown below, with reference to FIGS. 7–14.

Figures 7, 8:
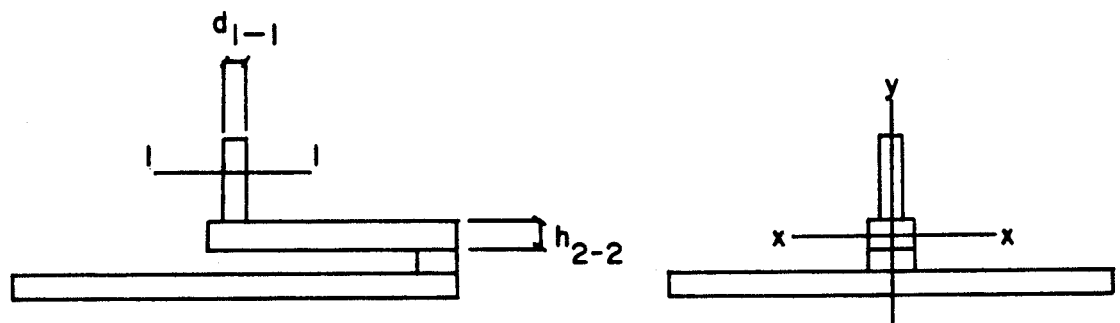
Figure 9:
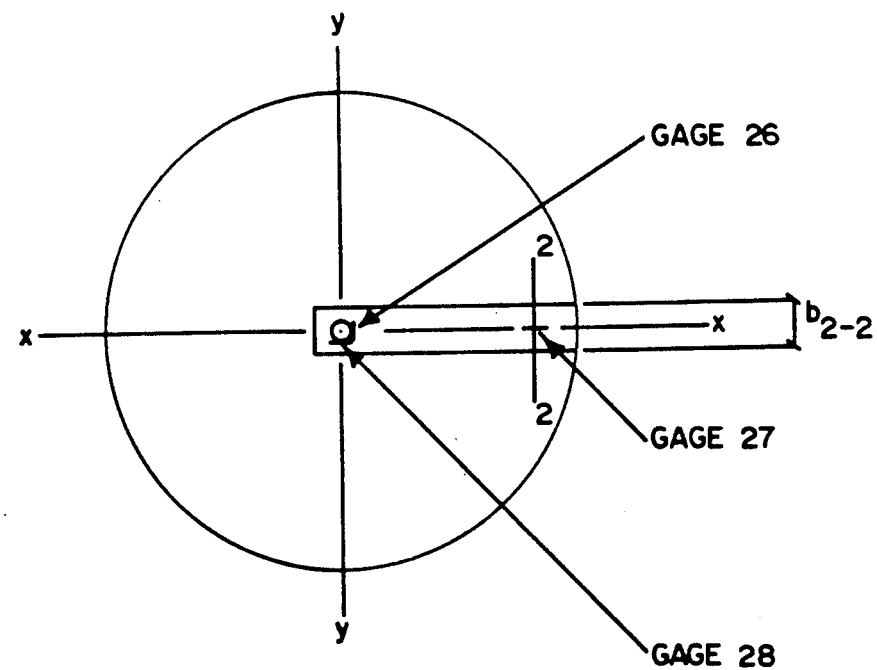

FIGS. 7–9 indicate positioning of the strain gauges used.

Analysis of Random Leadin of Pressure Plate vs. Force Application Readout, See FIGS. 7–9

$$\text{Stress} = \frac{P}{A} \pm \frac{M}{S}$$

$$\text{Strain} = \frac{\text{Stress}}{\text{Modulus of Elasticity}}$$

Figure 10:
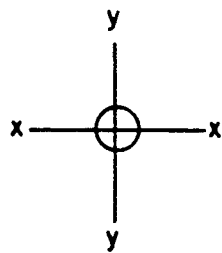

AT SECTION 1-1, See FIGS. 7 and 10

STRESS xx = Stress on the post due to a vertical load causing rotation about the X axis STRESS yy = Stress on the post due to a vertical load causing rotation about the Y axis.

Mxx = Moment about the X axis.

Myy = Moment about the Y axis.

P = Vertical force applied to the pressure plate

STRAINxx = Strain on the post due to a vertical load causing rotation about the X axis. Measured by gage 28.

STRAINyy = Strain on the post due to a vertical load causing rotation about the Y axis. Measured by gage 27.

$$S_{1-1} = \text{Section modulus} = \frac{\pi(d1-1)^3}{32}$$

E = Modulus of elasticity = 30,000,000 psi
$A_{1-1}$ = Area of post

Figure 11:
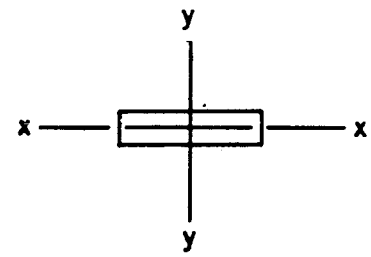

AT SECTION 2-2, See FIG. 11

STRESS$_{2-2}$ = Stress on cantilever bar due to a vertical load causing rotation about the X axis.

STRAIN$_{2-2}$=Strain on cantilever arm due to a vertical load causing rotation about the X axis.

$$S_{2-2} = \text{Section modulus} = \frac{b_{2-2}(h_{2-2})^2}{6}$$

$l_2$=Distance between the center of the post and where the cantilever arm hooks onto its support.

Mxx=Myy at section 1-1, Myy at section 1-1 is applied to the end of the cantilever arm.

Using stress and strain equations, a relationship between the three strain gages can be set up to calculate the force P applied to the pressure plate.

AT SECTION 1-1

$$STRESS_{yy} = STRAIN_{yy} \times E = \frac{P}{A_{1-1}} \pm \frac{M_{yy}}{S_{1-1}} = EQ \#1$$

$$STRESS_{xx} = STRAIN_{xx} \times E = \frac{P}{A_{1-1}} \pm \frac{M_{xx}}{S_{1-1}} = EQ \#2$$

AT SECTION 2-2

$$STRESS_{2-2} = STRAIN_{2-2} \times E = \frac{-Pl_2}{S_{2-2}} \pm \frac{M_{xx}}{S_{2-2}} = EQ \#3$$

STRAINyy, STRAINxx and STRAIN$_{2-2}$ are known from the strain gages $S_{2-2}$, $A_{1-1}$ and $S_{1-1}$ are constants that can be calculated. This leaves P, Mxx and Myy as unknowns. E is a constant that is looked up in a table. Using matrix algebra, the three unknowns can be solved for with the three equations above.

$$\frac{P}{A_{1-1}} + 0 + \frac{M_{yy}}{S_{1-1}} = STRAIN_{yy} \times E$$

$$\frac{P}{A_{1-1}} + \frac{M_{xx}}{S_{1-1}} 0 = STRAIN_{xx} \times E$$

$$\frac{-Pl_2}{S_{2-2}} + 0 + \frac{M_{xx}}{S_{2-2}} = STRAIN_{2-2} \times E$$

EQUATIONS OF FET SYSTEM
Properties

Figure 12:
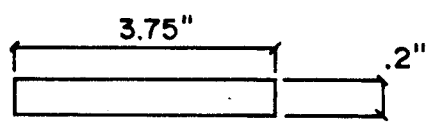

Cantilever arm, See FIG. 12

$$S_{2-2} = \frac{.375(.200)^2}{6} = 2.500(10)^{-3} \text{ IN}^3$$

CrossSection
$l_2 = 1.000$ IN

For C 1018 cold rolled steel $E = 30(10)^6$ PSI

-continued $$\frac{1}{S_{2-2}} = 400.000$$

Figure 13:

Threaded Post, See FIG. 13

$$S_{1-1} = \frac{\pi(.281)^3}{32} = 2.178(10)^{-3} \text{ IN}^3$$

$E = 30(10)^6$ psi $$A_{1-1} = \frac{\pi(.281)^2}{4} = 6.202(10)^{-2} \text{ IN}^2$$

$$\frac{1}{A_{1-1}} = \frac{1}{6.202(10)^{-2}} = 16.125$$

$$\frac{1}{S_{1-1}} = 459.137$$

EQUATIONS $16.125(P)+0+459.137(M_{yy})=30(10)^6(STRAIN_{yy})$ $16.125(P)+459.137(M_{xx})+0=30(10)^6(STRAIN_{xx})$ $400(P)+0+400.0(M_{xx})=30(10)^6(STRAIN_{2-2})$

Figure 14:
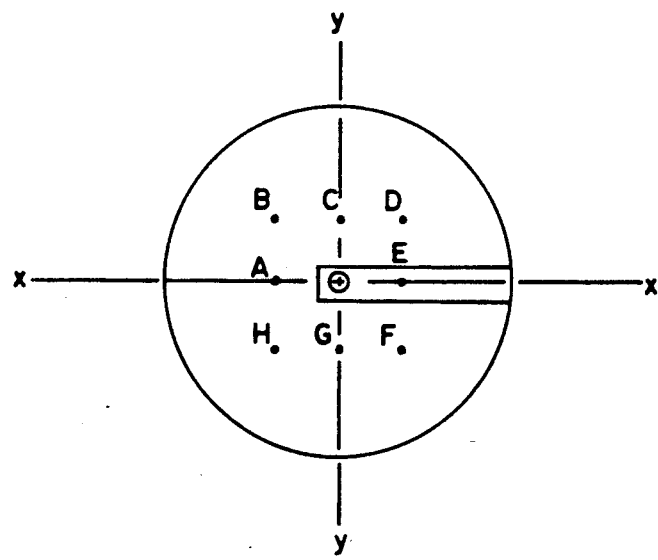

EXAMPLE OF CALCULATIONS, SEE FIG. 14
Directions

Moment lever arms are measured on an XY coordinate system. An example is point B. Its lever arm is $-1''$ in the X direction and $+1''$ in the Y direction.

EXAMPLE

Put A0.5# load at point A $M_{yy}=0.5\#(-1'')=-0.5\#-IN$ $M_{xx}=0$ At Section 1-1

$$STRESS_{yy} = E \times STRAIN_{yy} = \frac{P}{A_{1-1}} + \frac{M_{yy}}{S_{1-1}} =$$

$$\frac{.5}{6.202(10)^{-2}} + \frac{-.5}{2.178(10)^{-3}} = -221.506$$

$STRESS_{xx} = E \times STRAIN_{xx} =$ $$\frac{P}{A_{1-1}} + \frac{M_{xx}}{S_{1-1}} = \frac{.5}{6.202(10)^{-2}} + 0 = 8.062$$

$$STRESS_{2-2} = E \times STRAIN_{2-2} = \frac{-Pl_2}{S_{2-2}} + \frac{M_{xx}}{S_{2-2}} =$$

$$\frac{-.5(1)}{2.5(10)^{-3}} + \frac{-.5}{2.5(10)^{-3}} = -400$$

| Position | Calculated | | | | | | Equations | | |
| --- | --- | --- | --- | --- | --- | --- | --- | --- | --- |
| See Pg 5 | Load | Myy | Mxx | STRESS yy | STRESS xx | STRESS$_{2-2}$ | Load | Myy | Mxx |
| A | .5 | −.5 | 0 | −221.506 | 8.062 | −400 | .5 | −.5 | 0 |
| B | .5 | −.5 | .5 | −221.506 | 237.630 | −400 | .5 | −.5 | .5 |
| C | .5 | 0 | .5 | +8.062 | 237.630 | −200 | .5 | 0 | .5 |
| D | .5 | .5 | .5 | +237.630 | 237.630 | 0 | .5 | .5 | .5 |
| E | .5 | .5 | 0 | +237.630 | +8.062 | 0 | .5 | .5 | 0 |
| F | .5 | .5 | −.5 | +237.630 | −221.506 | 0 | .5 | .5 | −.5 |
| G | .5 | 0 | −.5 | +8.062 | −221.506 | −200 | .5 | 0 | −.5 |

| Position | Calculated | | | | | | Equations | | |
|---|---|---|---|---|---|---|---|---|---|
| See Pg 5 | Load | Myy | Mxx | STRESS yy | STRESS xx | STRESS$_{2\text{-}2}$ | Load | Myy | Mxx |
| H | .5 | −.5 | −.5 | −221.506 | −221.506 | −400 | .5 | −.5 | −.5 |

Using the calculated stresses in three simultaneous equations gives the same load used to calculate the stresses. Therefore the equations are correct.

Although a preferred form of my invention has been herein disclosed, it is to be understood that the present disclosure is by way of example and that variations are possible without departing from the subject matter coming within the scope of the following claims, which subject matter I regard as my invention.

I claim:

1. Transducer apparatus for use in testing muscle strength, comprising
   a housing having a rigid base plate;
   a substantially rigid support arm assembly mounted in the housing on said base plate and including a first leg affixed to said base plate and a substantially rigid second leg cantilevered from the first leg and having a longitudinal axis extending from said first leg a spaced distance from the base plate;
   a substantially rigid support post affixed to said second leg, said support post having an end portion projecting out of the housing and further having a longitudinal axis normal to the longitudinal axis through said second leg;
   a pressure plate affixed to the end of the support post projecting from said housing;
   first and second strain gauges, each having a longitudinal axis, and each mounted on the support post with its longitudinal axis parallel to the longitudinal axis of the post, said strain gauges mounted at ninety degrees with respect to each other around the longitudinal axis of the support post;
   a third strain gauge mounted on the second leg and having a longitudinal axis parallel to the axis of the second leg and in a plane in common with a plane that includes both the longitudinal axis of the second leg and the longitudinal axis of the support post;
   electrical means for converting signals output by all of said strain gauges into a signal indicative of muscle strength that contributes to the force exerted against said pressure plate when placed against a localized area of a person's body which is being activated by the person for diagnostic purposes; and
   means for displaying said signal indicative of muscle strength.

2. Apparatus for use in testing and measuring muscle strength as in claim 1, wherein
   the pressure plate has a surface curved to conform to a body portion of a user.

3. Apparatus as in claim 1, further including
   a cushion pad fixed to a face of the housing opposite to the pressure plate.

* * * * *

UNITED STATES PATENT AND TRADEMARK OFFICE
CERTIFICATE OF CORRECTION

PATENT NO. : 5,090,421

DATED : February 25, 1992

INVENTOR(S) : Earl V. Wagoner, III

It is certified that error appears in the above-identified patent and that said Letters Patent is hereby corrected as shown below:

Title page, items [19] and [75]:
The name of the inventor wherever it appears should be corrected from "Earl V. Wagoner, III" to "Earl Van Wagoner, III".

Column 2, Line 25, the word "date" should be "data".

Signed and Sealed this

Sixth Day of July, 1993

Attest:

MICHAEL K. KIRK

*Attesting Officer*     Acting Commissioner of Patents and Trademarks